(12) United States Patent
Huss

(10) Patent No.: US 7,850,710 B2
(45) Date of Patent: Dec. 14, 2010

(54) PUNCTURE CLOSURE APPARATUSES, SEALING PLUGS, AND RELATED METHODS

(75) Inventor: Brad D. Huss, Chanhassen, MN (US)

(73) Assignee: St. Jude Medical Puerto Rico LLC, Caguas, PR (US)

(*) Notice: Subject to any disclaimer, the term of this patent is extended or adjusted under 35 U.S.C. 154(b) by 393 days.

(21) Appl. No.: 11/419,941

(22) Filed: May 23, 2006

(65) Prior Publication Data

US 2007/0276433 A1 Nov. 29, 2007

(51) Int. Cl.
*A61B 17/08* (2006.01)
(52) U.S. Cl. ...................... 606/213; 606/232
(58) Field of Classification Search ................. 606/213, 606/232, 151, 157
See application file for complete search history.

(56) References Cited

U.S. PATENT DOCUMENTS

| | | | |
|---|---|---|---|
| 5,021,059 A | 6/1991 | Kensey et al. | |
| 5,192,300 A | 3/1993 | Fowler | |
| 5,290,310 A | 3/1994 | Makower et al. | |
| 5,312,435 A | 5/1994 | Nash et al. | |
| 5,383,896 A | 1/1995 | Gershony et al. | |
| 5,437,631 A | 8/1995 | Janzen | |
| 5,476,469 A | 12/1995 | Hathaway et al. | |
| 5,507,744 A | 4/1996 | Tay et al. | |
| 5,531,755 A | 7/1996 | Smith et al. | |
| 5,531,759 A * | 7/1996 | Kensey et al. | 606/213 |
| 5,545,178 A | 8/1996 | Kensey et al. | |
| 5,662,681 A | 9/1997 | Nash et al. | |
| 5,700,277 A | 12/1997 | Nash et al. | |
| 5,707,393 A * | 1/1998 | Kensey et al. | 606/213 |
| 5,720,757 A | 2/1998 | Hathaway et al. | |
| 5,741,223 A | 4/1998 | Janzen et al. | |
| 5,830,130 A | 11/1998 | Janzen et al. | |
| 5,861,004 A | 1/1999 | Kensey et al. | |
| 5,906,631 A | 5/1999 | Imran | |
| 5,935,147 A | 8/1999 | Kensey et al. | |
| 6,007,563 A * | 12/1999 | Nash et al. | 606/213 |
| 6,024,756 A * | 2/2000 | Huebsch et al. | 606/213 |
| 6,045,569 A | 4/2000 | Kensey et al. | |
| 6,048,358 A | 4/2000 | Barak | |
| 6,090,130 A | 7/2000 | Nash et al. | |
| 6,126,675 A | 10/2000 | Shchervinsky et al. | |
| 6,179,863 B1 | 1/2001 | Kensey et al. | |
| 6,261,309 B1 | 7/2001 | Urbanski | |
| 6,312,446 B1 * | 11/2001 | Huebsch et al. | 606/213 |

(Continued)

*Primary Examiner*—(Jackie) Tan-Uyen T. Ho
*Assistant Examiner*—Jing Rui Ou
(74) *Attorney, Agent, or Firm*—Holland & Hart

(57) ABSTRACT

A puncture closure device is disclosed. Particularly, a puncture closure device may include an anchor support including a coupling feature and an anchor connected to the anchor support. Further, the puncture closure device may include a movable compression element configured to compress a sealing plug generally between the compression element and the anchor. Such a puncture closure device may be positioned at least partially within an insertion sheath to form a puncture closure assembly. A method of compressing a sealing plug and a method of sealing a puncture are disclosed. In addition, in one embodiment, a sealing plug may comprise a first, a second, and an intermediate end region, wherein the intermediate region has a density less than the first and second end regions. In another embodiment, a sealing plug may include a bore formed therethrough and a plurality of slits formed into an exterior surface of the sealing plug.

24 Claims, 15 Drawing Sheets

U.S. PATENT DOCUMENTS

| | | | |
|---|---|---|---|
| 6,425,911 B1 * | 7/2002 | Akerfeldt et al. | 606/213 |
| 6,547,806 B1 | 4/2003 | Ding | |
| 6,682,489 B2 | 1/2004 | Tenerz et al. | |
| 2005/0085852 A1 * | 4/2005 | Ditter | 606/213 |

* cited by examiner

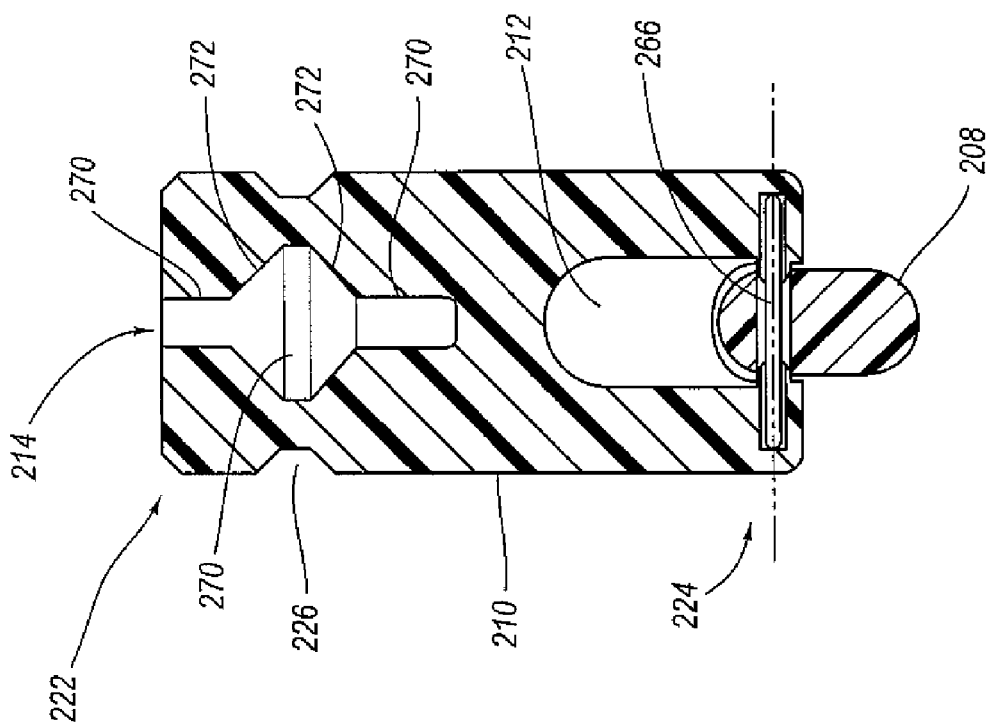
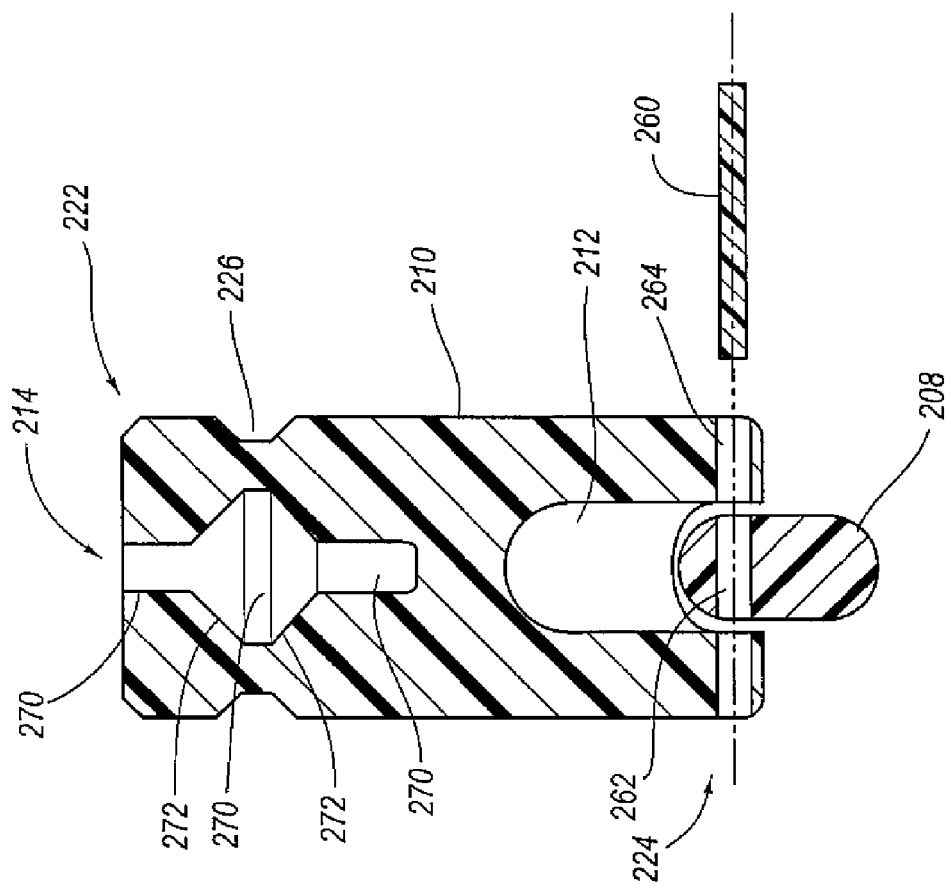
Fig. 8
Fig. 7

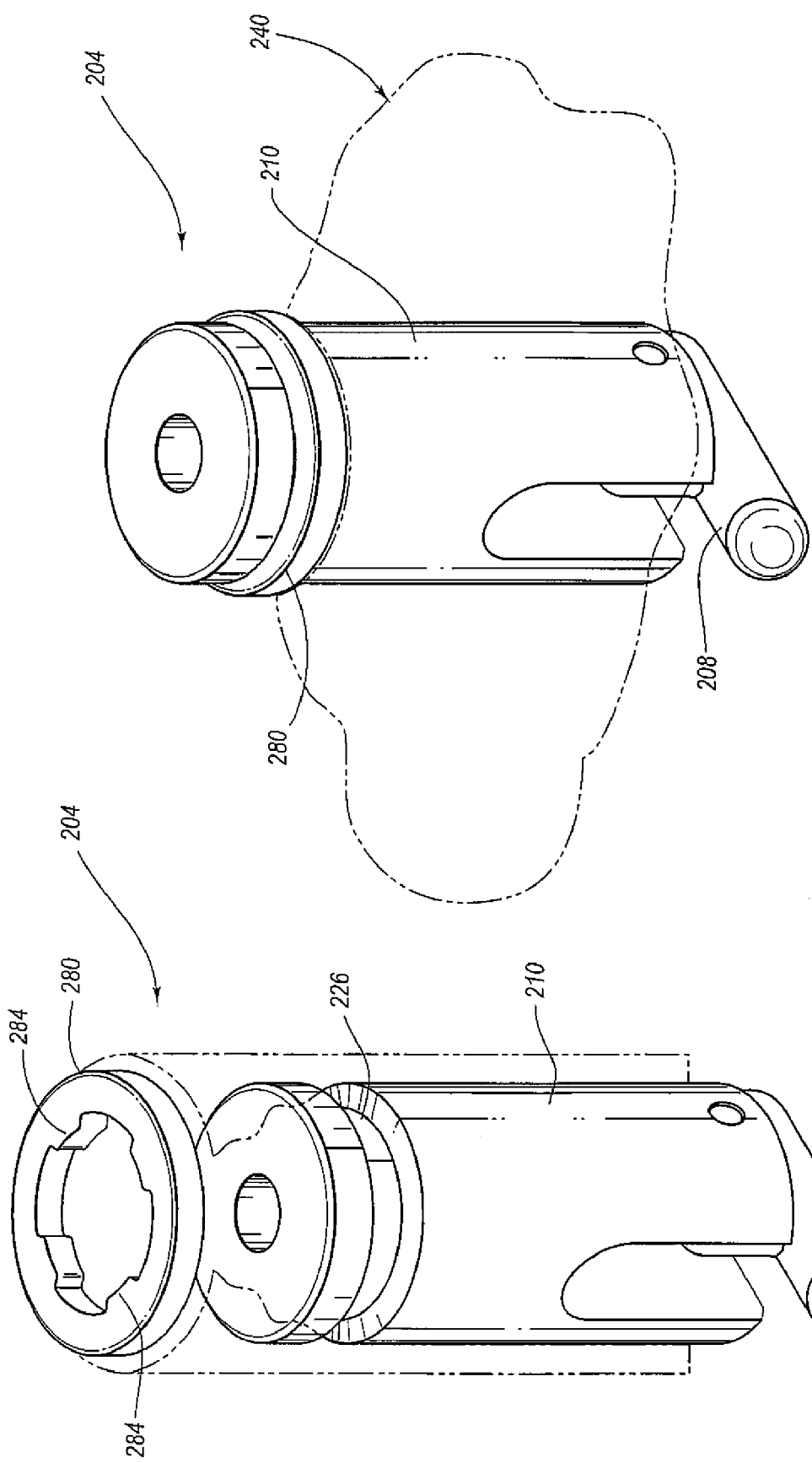

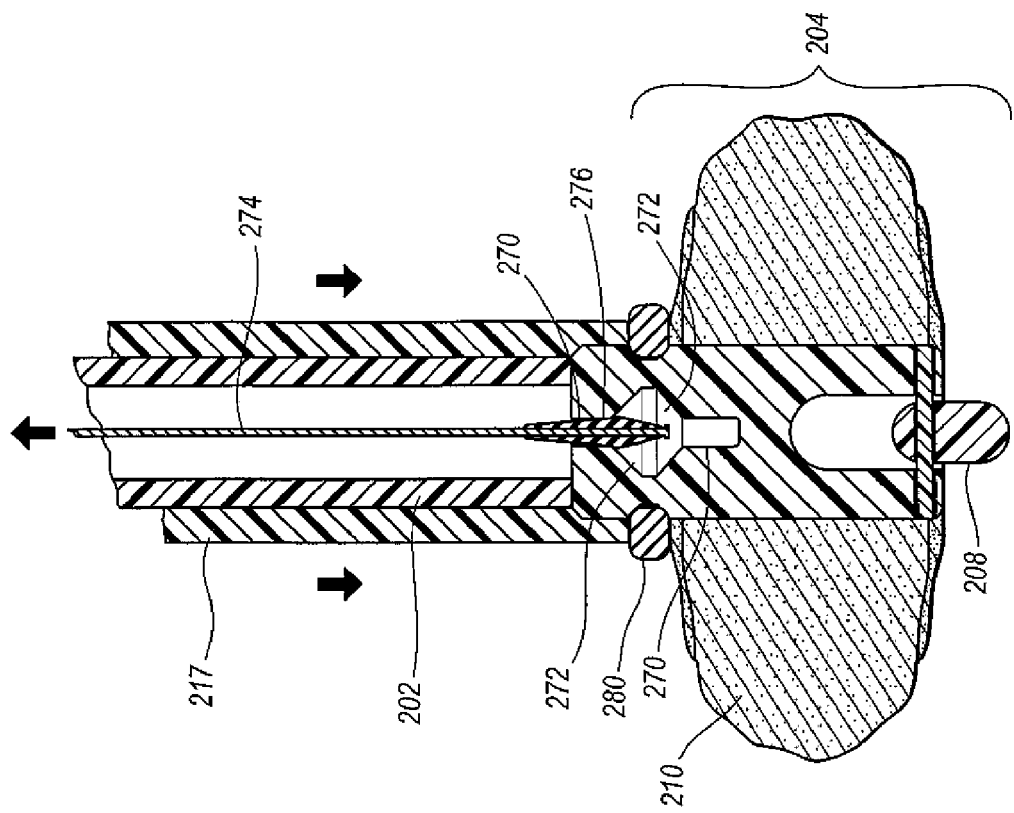
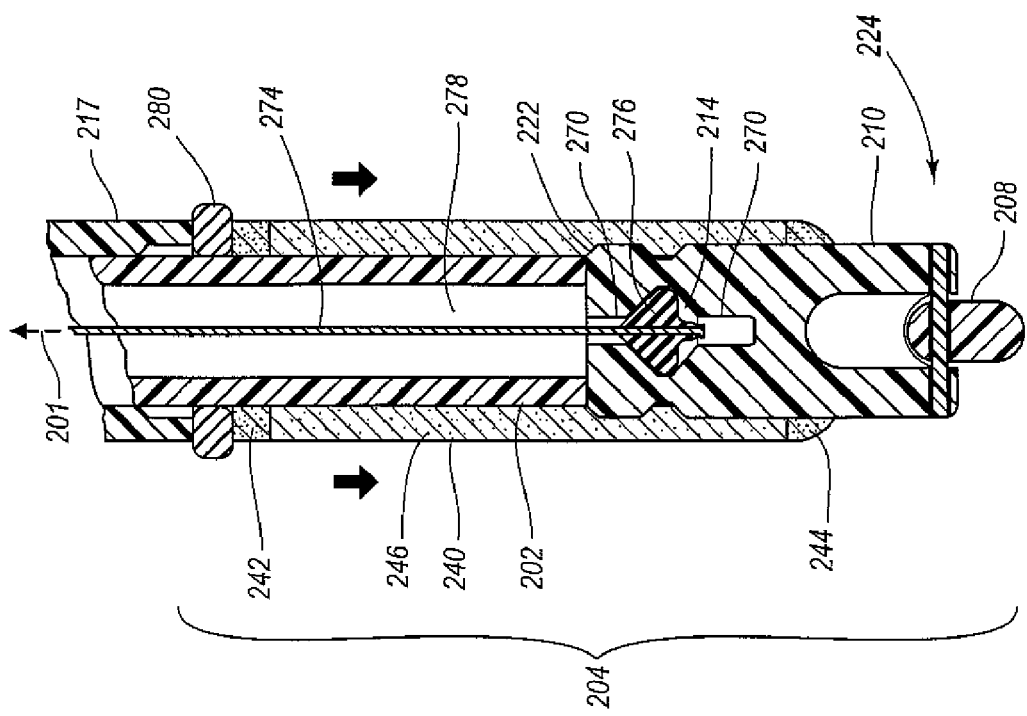

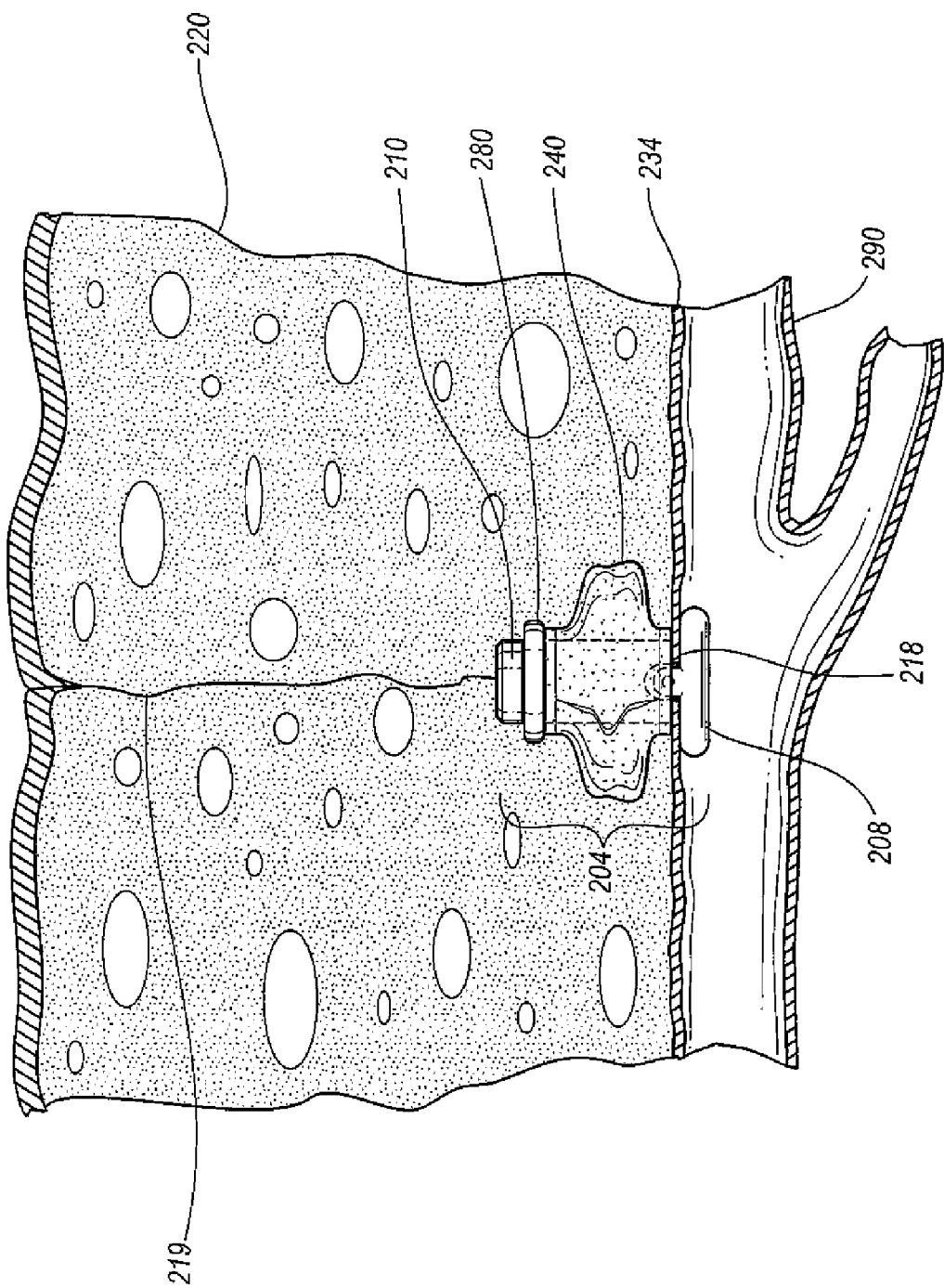

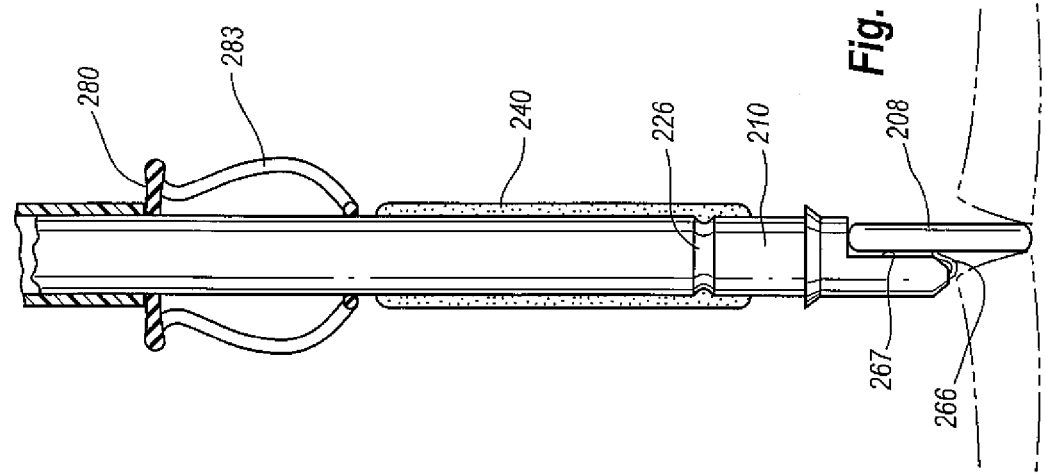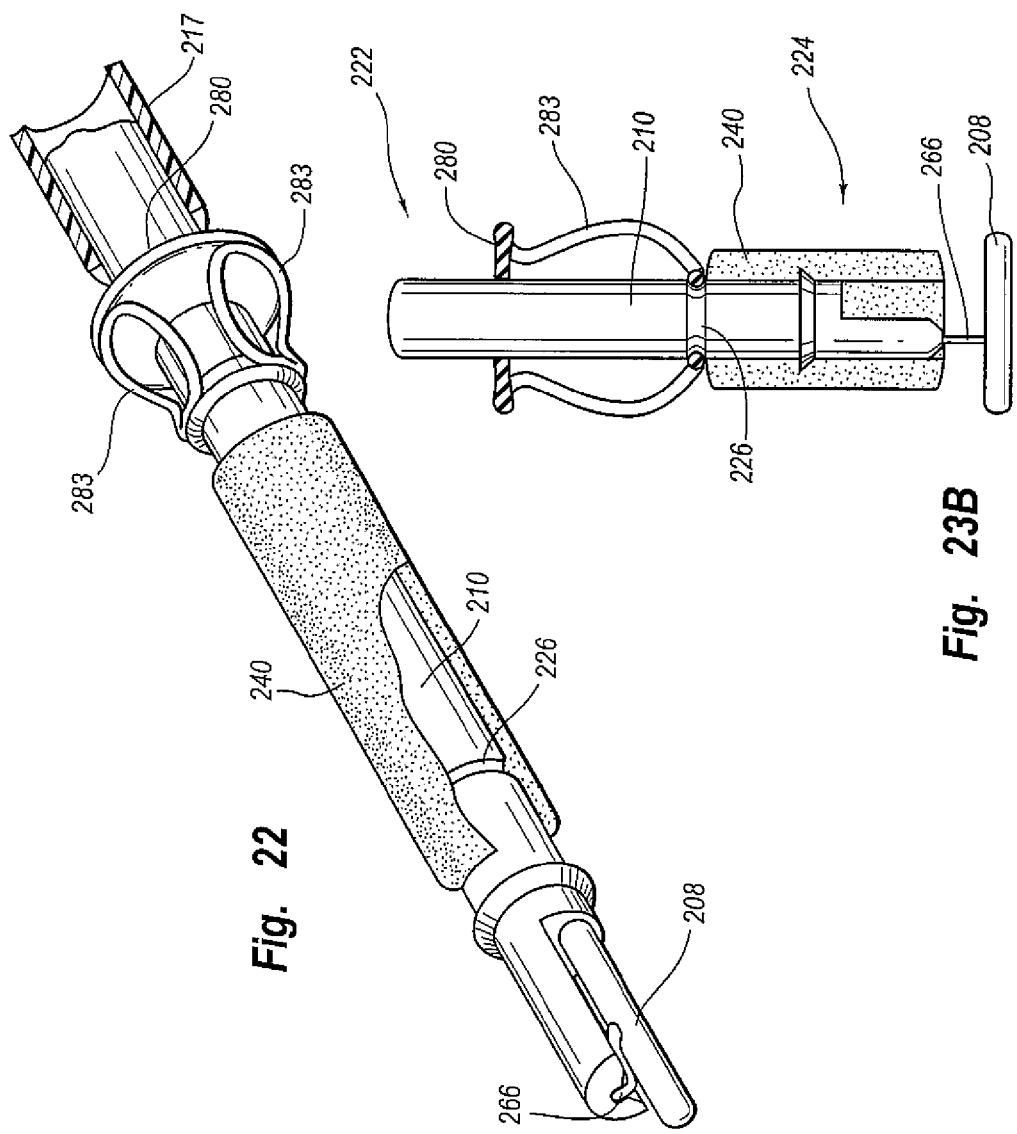

PUNCTURE CLOSURE APPARATUSES, SEALING PLUGS, AND RELATED METHODS

TECHNICAL FIELD

This relates generally to medical devices and more particularly to methods and devices for sealing punctures or incisions in a tissue wall

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963; 6,090,130; and 6,045,569 and related patents, which are hereby incorporated by this reference.

Typical closure devices such as the ones described in the above-mentioned patents place a sealing plug at the tissue puncture site. Nevertheless, the incision track leading to the invaded artery often continues to ooze blood from side vessels at the puncture site. Manual compression is typically applied at the puncture site to stop the track bleeding. Manual compression can lead to patient soreness and requires additional time from medical personnel. The time spent by medical personnel compressing the puncture site to stop the bleeding from the incision track can be expensive to the patient, and tiring to the medical personnel. Accordingly, there is a need for improving the sealing methods and apparatus at the site of subcutaneous tissue punctures.

SUMMARY OF THE INVENTION

One aspect of the present invention relates to a puncture closure device. Particularly, a puncture closure device may include an anchor support including a coupling feature and an anchor connected to the anchor support, wherein the anchor is configured for insertion through a puncture. Further, the puncture closure device may include a movable compression element configured to be movable between a first position and a second position, wherein movement of the compression element to the second position causes coupling of the compression element to the coupling feature of the anchor support and a sealing plug positioned generally between the compression element and the anchor. The compression element may be configured to cause compression of the sealing plug generally between the compression element and the anchor upon movement of the compression element from the first position to the second position. A puncture closure assembly may comprise a puncture closure device and an insertion sheath configured to receive at least a portion of the puncture closure device.

Another aspect of the present invention relates to a method of compressing a sealing plug. Particularly, a bore of a sealing plug may be positioned generally about a portion of an anchor support, wherein the anchor support is connected to an anchor and the sealing plug may be longitudinally compressed. A further aspect of the present invention relates to a method of sealing a puncture. More specifically, an anchor may be positioned generally within a puncture, the anchor connected to an anchor support. Further, a bore of a sealing plug may be positioned generally about a portion of an anchor support. In addition, the sealing plug may be longitudinally compressed generally between the anchor and a compression element.

An additional aspect of the present invention relates to a sealing plug for use in a puncture closure apparatus. In one embodiment, a sealing plug may comprise a first end region, a second end region, and an intermediate region positioned between the first end region and the second end region, wherein the intermediate region comprises a material with a density less than a density of the first end region and a density of the second end region. In another embodiment a sealing plug may comprise a generally cylindrical body including a bore formed therethrough and a plurality of slits formed into an exterior surface of the sealing plug, the plurality of slits configured to facilitate radial expansion of the sealing plug in response to longitudinal compression of the sealing plug.

Features from any of the above mentioned embodiments may be used in combination with one another, without limitation. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Further features of the subject matter of the present invention, its nature, and various advantages will be more apparent from the following detailed description and the accompanying drawings, which illustrate various exemplary embodiments, are representations, and are not necessarily drawn to scale, wherein:

FIG. 7 shows a side cross-sectional view of one embodiment of an anchor and a anchor support, wherein the anchor is pinned to the anchor support;

FIG. 8 shows a side cross-sectional view of another embodiment of an anchor and an anchor support, wherein the anchor is pivotably coupled to the anchor support by a suture;

FIG. 15 shows a perspective view of a plug assembly prior to deployment according to the invention;

FIG. 16 shows a perspective view of the plug assembly shown in FIG. 15 after deployment;

FIG. 17 shows a partial side cross-sectional view of a puncture closure device during use;

FIG. 18 shows a partial side cross-sectional view of a puncture closure device shown in FIG. 17, wherein the sealing plug has been longitudinally compressed and radially expanded; and FIG. 19 shows perspective view of a plug assembly deployed partially within a tissue tract and partially within a blood vessel to effectively close a puncture formed in the blood vessel.

FIG. 22 is perspective view of another embodiment of a puncture closure device prior to deployment.

FIGS. 23A and 23B illustrate stages of deployment of the puncture closure device shown in FIG. 22.

Throughout the drawings, identical reference numbers designate similar, but not necessarily identical, elements.

DETAILED DESCRIPTION

Figure 1:
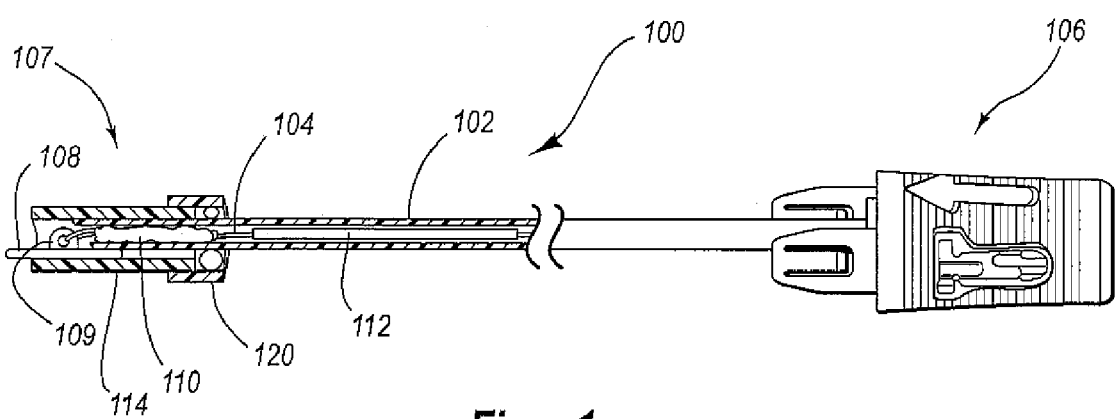
FIG. 1 shows a side view, partly in section, of a conventional puncture closure device.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for elongated bleeding. The present disclosure describes methods and apparatus that facilitate placement and sealing of tissue punctures. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a puncture closure device, the methods and apparatus are only limited by the appended claims.

The term "tissue," as used herein, means an aggregation of morphologically similar cells and associated intercellular matter acting together to perform one or more specific functions in a body. The term "lumen," as used herein, means any open space or cavity in a bodily organ, especially in a blood vessel. The terms "tamp" or "tamping," as used herein, mean pushing or packing by one or a succession of pushes, blows, or taps. The term "biologically resorbable material," as used herein, means a material capable of degradation by biological processes such as collagen, synthetic collagen, polymerized polylactic acid, polyglycolic acid matrix, or any other bioabsorbable material. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4). The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Figure 2:
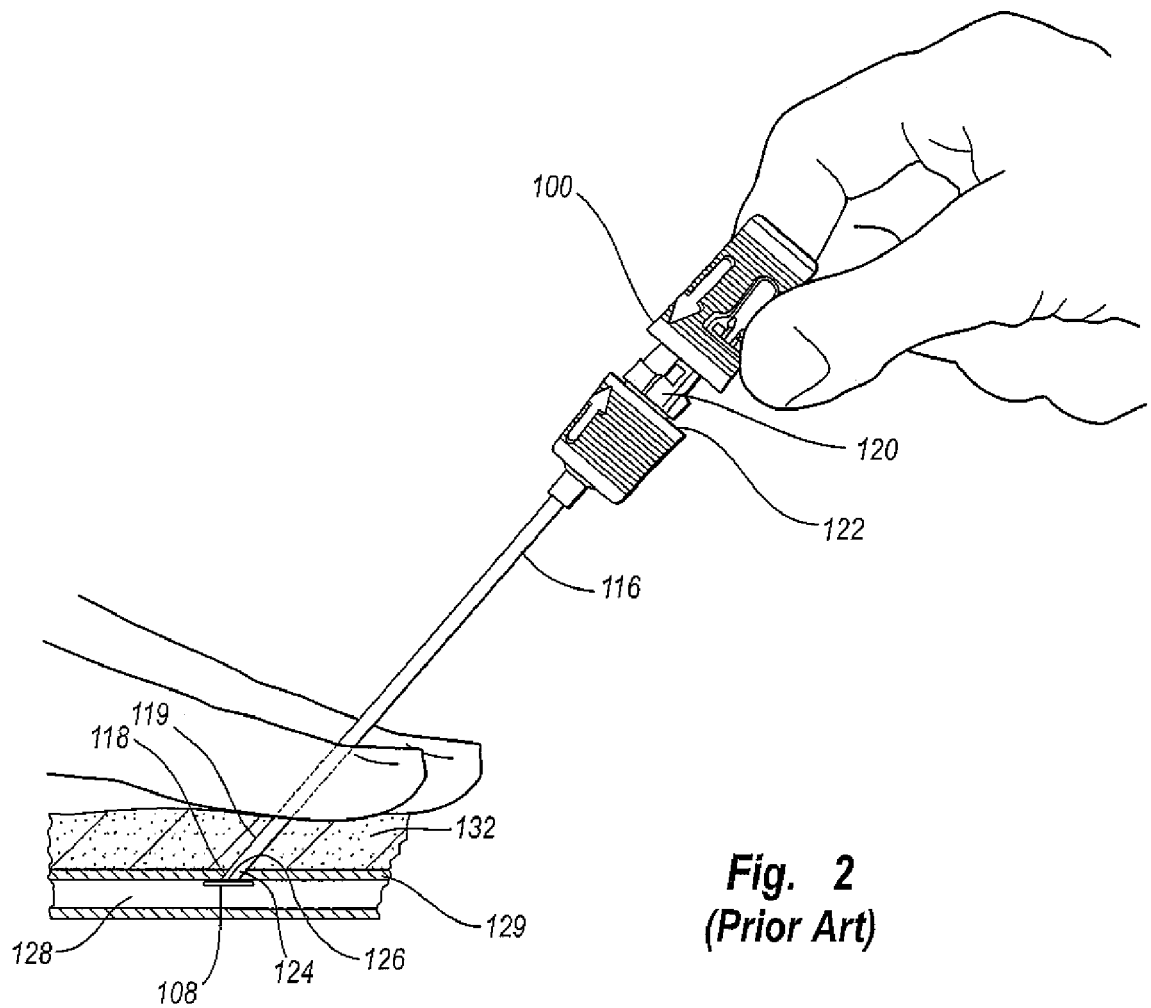
FIG. 2 shows a schematic side view of the puncture closure device shown in FIG. 1 inserted through an insertion sheath and engaged with a blood vessel.
Figure 3:
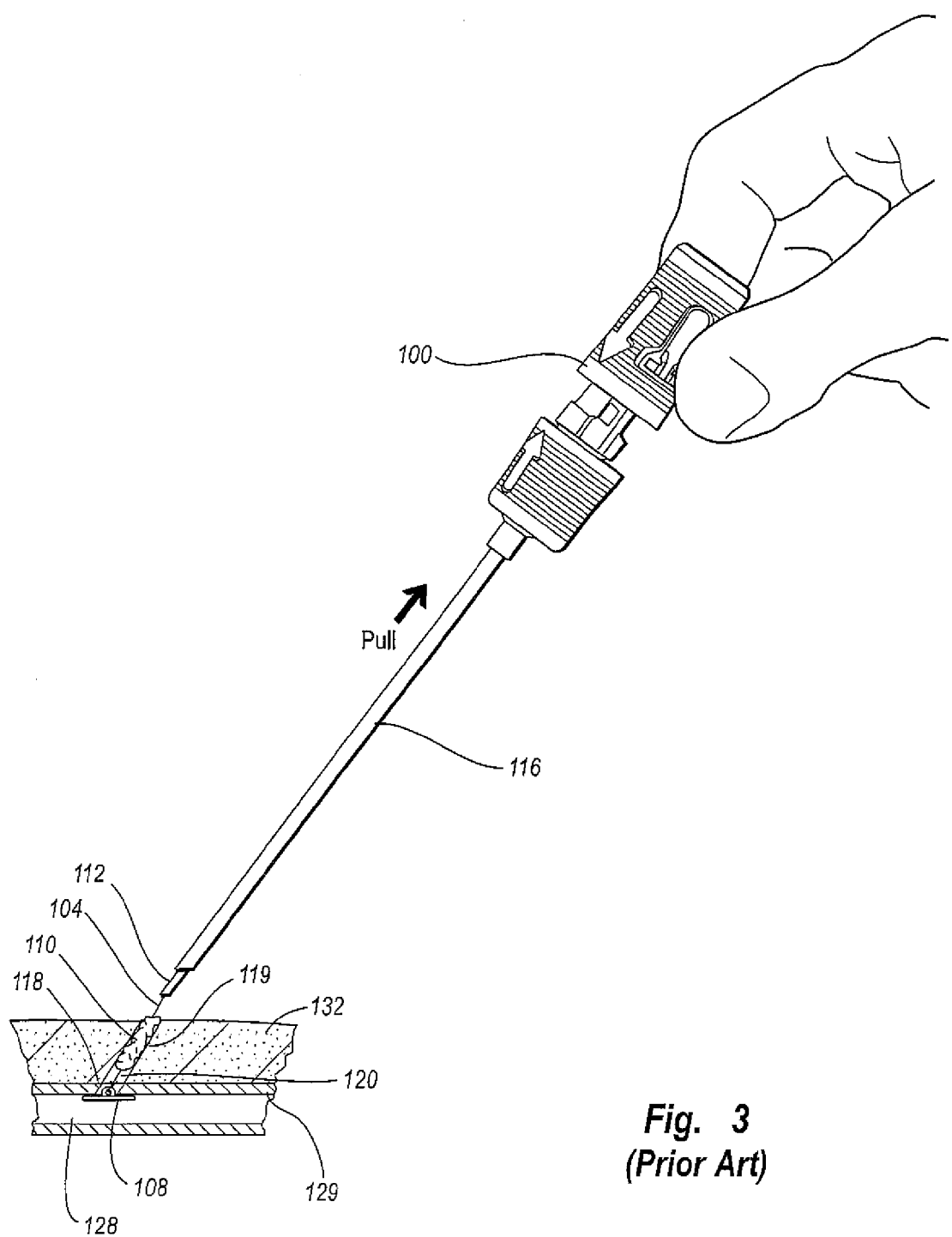
FIG. 3 shows a schematic side view of the conventional puncture closure device as shown in FIG. 2, wherein the conventional puncture closure device and insertion sheath are being withdrawn from the artery to deploy a sealing plug.
Figure 4:
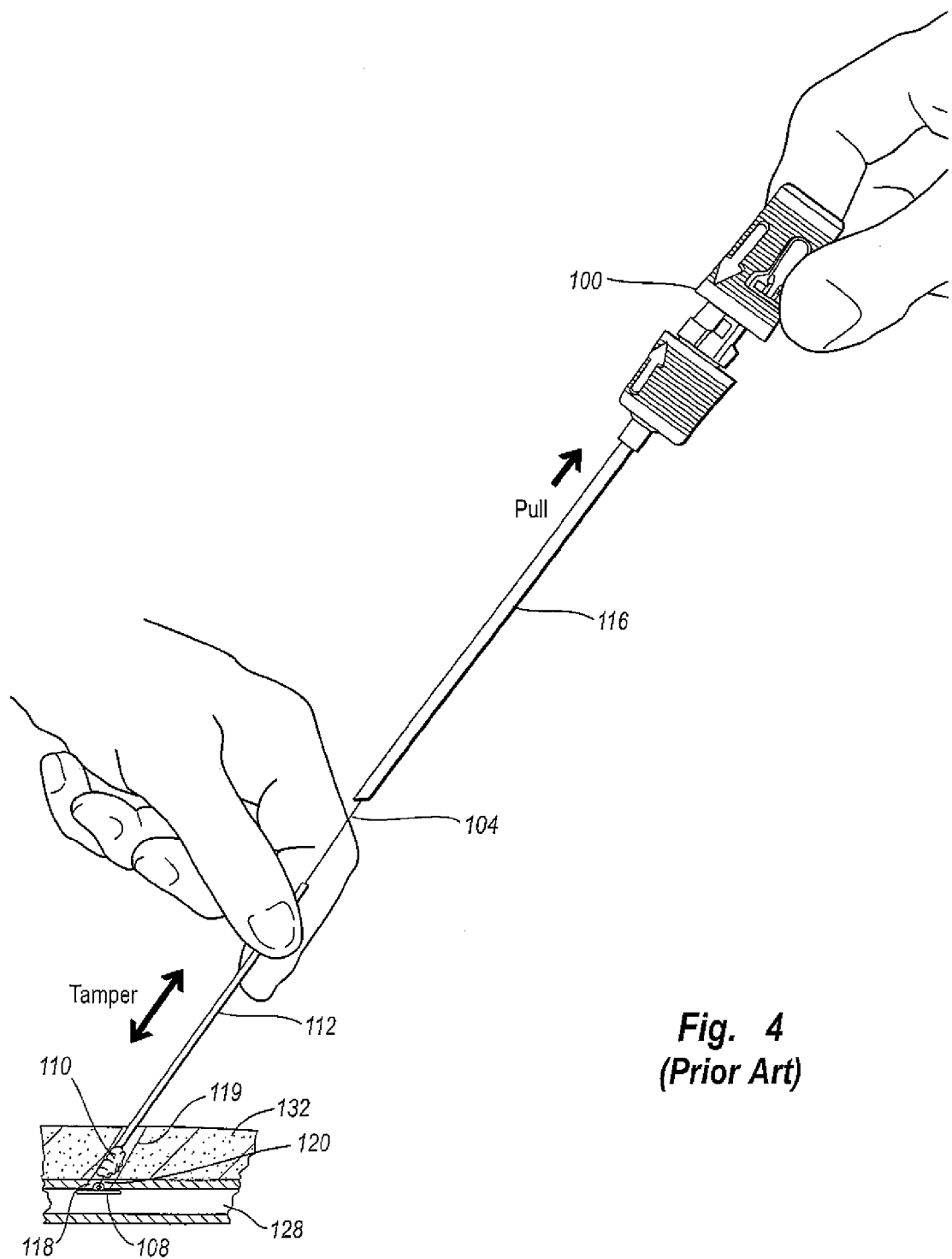
FIG. 4 shows a side view of the conventional puncture closure device, as shown in FIG. 3, illustrating use of a tamping tube to tamp the sealing plug.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102. The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, however, it may be difficult to adequately tamp the collagen pad 110. Tamping cannot commence until the sheath 116 has been removed so as to expose the tamping tube 112 for manual grasping. Under certain conditions, removal of the sheath 116 prior to tamping the collagen pad 110 causes the collagen pad 110 to retract or displace proximally from the tissue puncture 118, creating an undesirable gap 120 between the collagen pad 110 and the puncture 118. The gap 120 may remain even after tamping as shown in FIG. 4, and sometimes results in only a partial seal and bleeding from the tissue puncture 118.

Therefore, the present specification describes an methods and apparatuses including a tissue puncture closure device that may provide a stable seal at the tissue puncture site. The tissue puncture closure device may include an anchor attached to a rigid support with a sealing plug movably disposed thereover.

Generally, one aspect of the present invention described herein relates to a puncture closure device including a movable compression element configured to compress and deform a sealing plug within a tissue tract of a patient. More particularly, in one embodiment, a puncture closure device may include an anchor, an anchor support, and a movable compression element. Further, the movable compression element may be configured to compress the sealing plug and lock, contact, or couple to the anchor support upon moving to a selected position. Such a configuration may provide repeatability in the compression of the sealing plug and may provide a relatively unobtrusive closure assembly which may be deployed within a patient.

Figure 5:
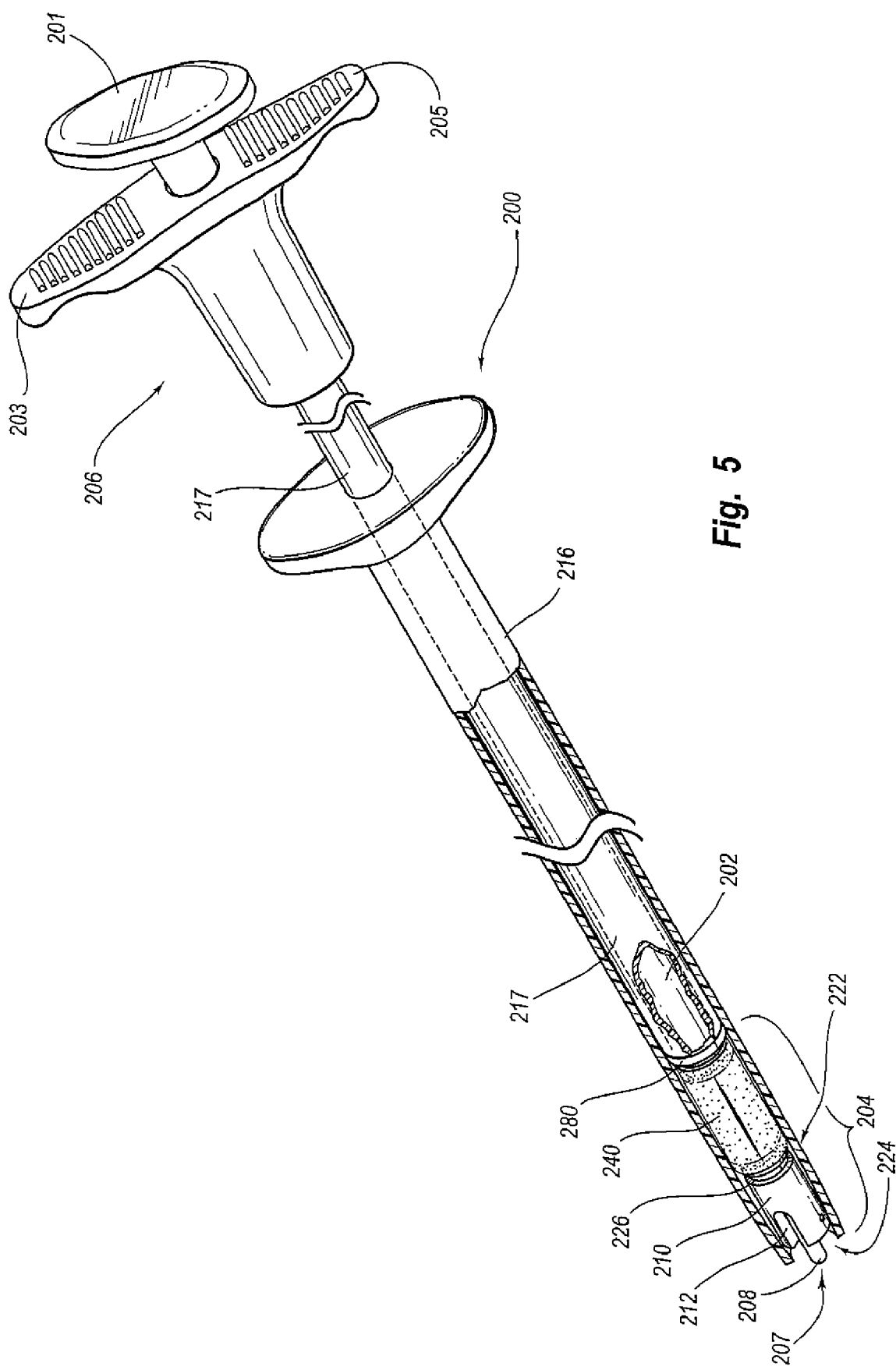
FIG. 5 shows a schematic perspective view of a puncture closure device according to the present invention.

FIG. 5 shows one embodiment of a puncture closure device 200 according to principles of the present invention. The puncture closure device 200 may have particular utility when used in connection with intravascular procedures, such as angiographic dye injection, cardiac catheterization, balloon angioplasty and other types of vascular access of atherosclerotic arteries, etc., as may be appreciated with respect to use of the puncture closure device 200 to effectively close vascular incisions as described below. However, it will be understood that while the description of the embodiments below are directed to closure of percutaneous punctures in blood vessels, such devices have much more wide-spread applications and can be used for sealing punctures or incisions in other types of tissue walls and tissues as well. Thus, the sealing of a percutaneous puncture in a blood vessel, as shown and discussed herein, is merely illustrative of one particular application of the apparatuses and methods of the present invention.

Figure 6:
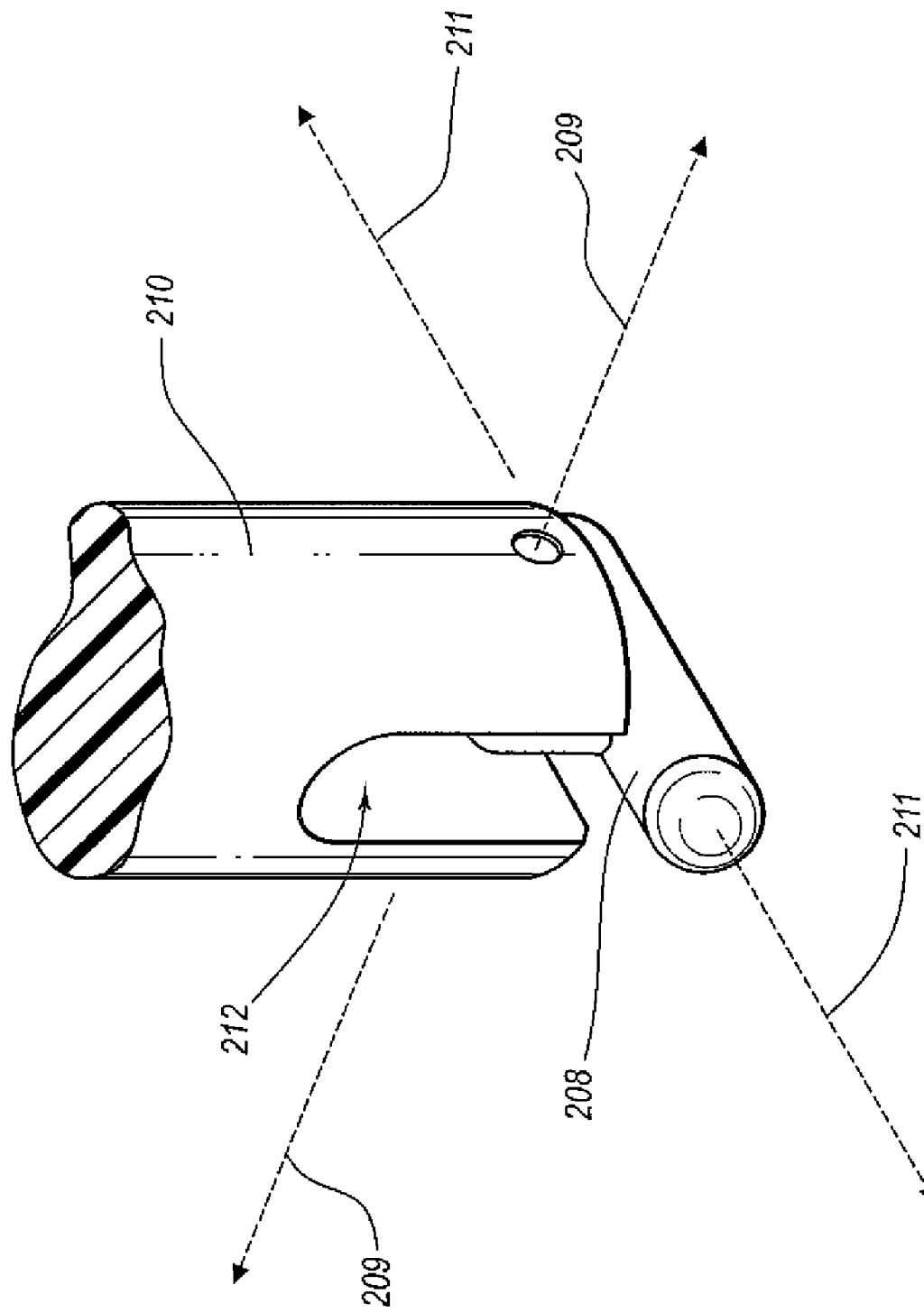
FIG. 6 shows a perspective view of one embodiment of an assembly of an anchor and an anchor support.

As shown in FIG. 5, the puncture closure device 200 includes a proximal end 206 and a distal end 207. A plug assembly 204 is positioned generally near the distal end 207 and includes an anchor 208, an anchor support 210, a coupling feature 226, a sealing plug 240, and a compression element 280. The sealing plug 240 may comprise any biologically resorbable material (e.g., collagen, polyglycolic acid, etc.), as known in the art. For example, sealing plug 240 may comprise a sponge-like material (e.g., naturally occurring collagens, synthetic collagens, or other biologically resorbable sponge-like material), a foam, or a fibrous material, and may be configured in any shape to facilitate sealing the puncture 218. The sealing plug may also include a hemostatic agent, such as a tissue thromboplastin, to accelerate local hemostasis. Anchor support 210 includes a proximal end 222 and distal end 224 which, optionally, may be coincident with the distal end 207 of the closure device 200. As shown in FIG. 5, the anchor 208 is positioned at least partially within a recess 212 of the anchor support 210 to facilitate insertion into a lumen of a blood vessel. In further detail, FIG. 6 shows a perspective view of anchor support 210 and anchor 208 according to one embodiment. Anchor 208 may be pivotably coupled to anchor support 210. Put another way, anchor 208 may be coupled to anchor support 210 so that anchor 208 may pivot generally about an axis of rotation 209. As shown in FIG. 6, anchor 208 includes a body that is elongated along an axis of elongation 211, which, optionally, may be oriented substantially perpendicularly with respect to axis of rotation 209. Of course, many different embodiments for anchor 208 and anchor support 210 are contemplated by the present invention. For example, FIGS. 7, 8, 20, and 22 show different embodiments of an assembly including an anchor and an anchor support. In one embodiment, anchor 208 may be coupled to the anchor support 210 with a pin 260 shown in FIG. 7. Pin 260 passes through a hole 264 formed through anchor support 210 and an eyelet aperture 262 formed through a portion of anchor 208. In another embodiment shown in FIG. 8, anchor 208 may be coupled to the anchor support 210 with a suture 266 or any other relatively flexible member which can be attached or molded to the anchor support 210. In the separate embodiments shown in of FIGS. 20 and 22, anchor support 210 may have the suture 266 attached or molded to a distal end 224. The suture 266 attaches the anchor support 210 to the anchor 208. The anchor 208 may be initially arranged in a nest 267 formed in the anchor support 210 at the distal end 224.

In the embodiments of FIGS. 7, 8, 20, and 22, the anchor 208 may be configured to be positioned inside a blood vessel and against a wall of the blood vessel. Further, the anchor 208 may be configured to be generally centered with respect to a puncture formed through a wall of a blood vessel. The anchor 208 may comprise an elongated, low-profile member (i.e., with respect to a distance inwardly from the wall of a blood vessel) and may comprise a relatively stiff (e.g., exhibiting a relatively high modulus of elasticity) material. In addition, the anchor 208 may comprise a biologically resorbable material such as, for example, a mixture of approximately 50% lactide and 50% glycolide material. The anchor support 210 may also comprise a biologically resorbable material such as, for example, collagen or polyglycolic acid (PGA).

As shown the embodiments of FIGS. 7, 8, 20, and 22 anchor support 210 includes first or proximal end 222 and second or distal end 224. Coupling feature 226 (shown in FIGS. 7, 8, 20 and 22 as an annular groove) may be located near first end 222 of anchor support 210. Anchor support 210 tends to hold its shape and may be substantially rigid. Anchor support 210 defines a rigid support to which the anchor 208 is mounted. Anchor support 210 may be referred to as a rigid support member and have a rigid portion. Anchor support 210 is shown in at least FIG. 7 having a generally elongate construction and may be referred to as a generally rigid elongated member. Anchor support 210 comprises a bioabsorbable material and may include a hemostasis promoting material. Generally, coupling feature 226 may be configured for selectively engaging an associated coupling feature of a movable compression element, as described in greater detail below. As shown in FIGS. 7, 8, 20 and 22, the coupling feature 226 may be a groove indented into anchor support 210 that is substantially concentric with respect to the body of anchor support 210 and may be positioned anywhere along the outside surface of the anchor support. In the embodiments of FIGS. 7, 8, 20 and 22 the coupling feature 226 is arranged proximate to the first end 222 of the anchor support 210. Thus, it may be appreciated that in some embodiments, a mating device such as suitably sized retaining ring or disc-shaped member may be moved along the first end 222 of anchor support 210 and positioned at least partially within coupling feature 226. It should be noted that the retaining ring or disc-shaped member is not necessarily closed, it may comprise a partial ring or disc. Such a configuration may effectively couple the suitably sized ring or disc to the coupling feature 226. Of course, many different interlocking, coupling, contacting, and engaging structures (e.g., tabs, slots, threads, protrusions, recesses, snap-fittings, etc.) may be employed as a coupling feature 226 in cooperation with an associated coupling feature of a mating device such as a movable compression element (discussed below).

As further shown in FIGS. 7 and 8, anchor support 210 may optionally include a cavity 214 defining an opening at the first end 222 of anchor support 210 that extends toward second end 224. In one embodiment, cavity 214 may include one or more substantially cylindrical regions 270 and one or more non-cylindrical regions 272. Non-cylindrical regions 272 may be substantially conical or substantially spherical in shape. The non-cylindrical regions 272 may form diverging/converging cones as shown in FIGS. 7 and 8.

Figure 20:
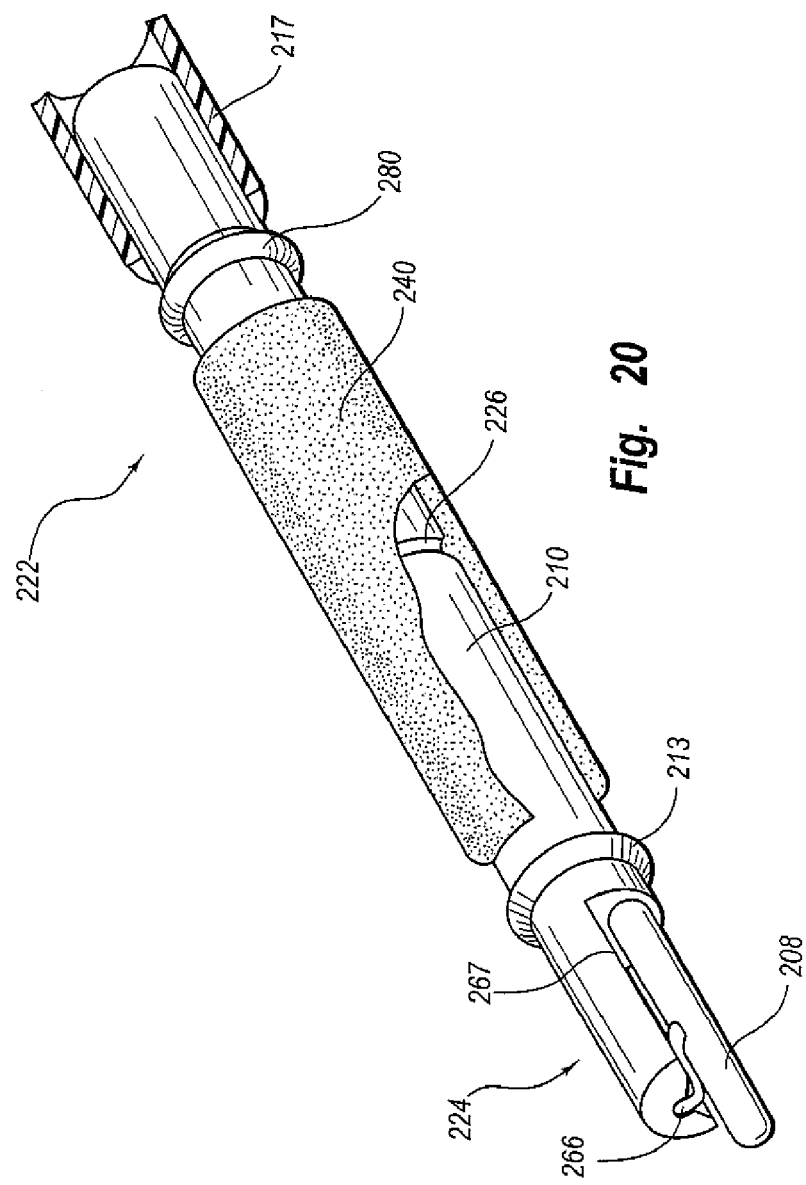
FIG. 20 is a perspective view of another embodiment of a puncture closure device prior to deployment.
Figure 21D:
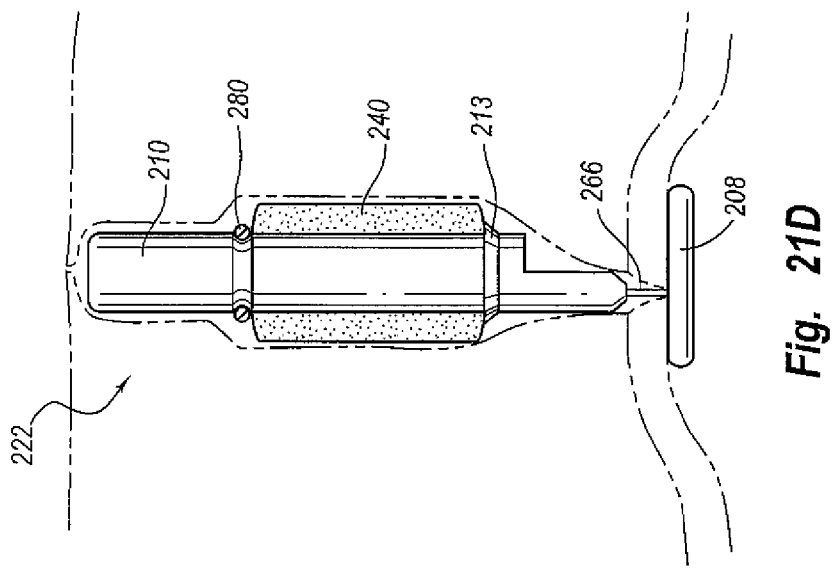
FIGS. 21B-21D illustrate stages of deployment of the puncture closure device shown in FIG. 21A.
Figure 21C:
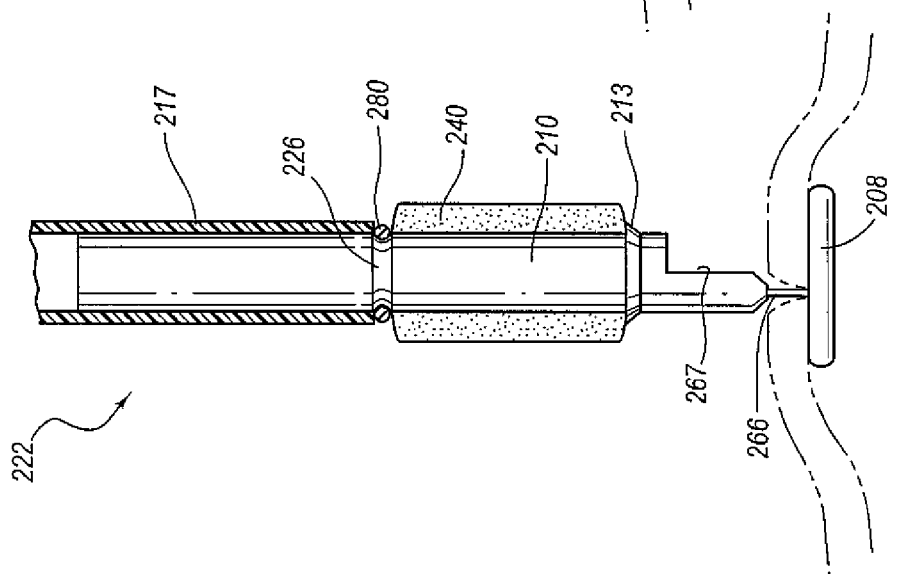
Figure 21B:
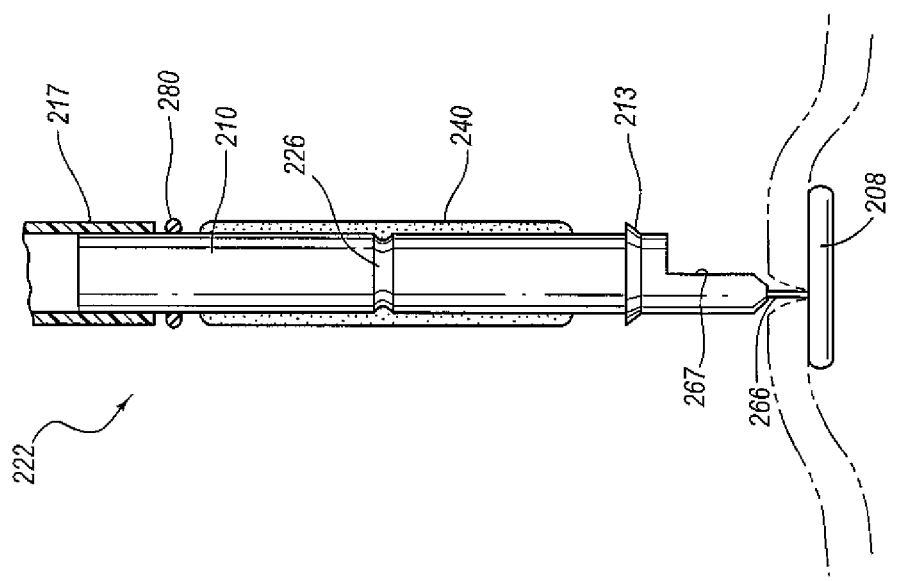

Referring again to FIG. 5, prior to deployment of the plug assembly 204 within a tissue tract, the anchor support 210 may be positioned adjacent to a placement rod 202 at the first end 222 of the anchor support 210. Sealing plug 240 may be initially substantially concentrically positioned with respect to placement rod 202 as shown in FIG. 5, and may also be slidably connected or radially adjacent to anchor support 210 as shown in FIGS. 20 and 22. Put another way, a bore may be formed through sealing plug 240 and placement rod 202 or anchor support 210 may be positioned within the bore of the sealing plug 240. Optionally, sealing plug 240 may at least partially interfere (i.e., an interference fit) with the exterior of placement rod 202 or anchor support 210 to provide a snug fit such that the sealing plug 240 tends to remain in place until acted upon by a force exceeding the frictional force between the sealing plug 240 and the placement rod 202 or the anchor support 210. However, a compression element such as a slideable collar 280 may be arranged around the placement rod 202 or the anchor support 210 proximal of the sealing plug. The slideable collar 280 can be moved to cause movement and/or compression of the sealing plug 240 as discussed in more detail below.

Further, placement rod 202 may extend from the first end 206 of the puncture closure device 200 to the anchor support 210 through a tamper 217 and through a sheath 216. Tamper 217 is also positioned within sheath 216 and abuts slideable collar 280. Tamper 217 has an outer diameter that is larger than an inner diameter of the slideable collar 280 (or an inner diameter that is smaller than an outer diameter of the slideable collar 280) so that an operator may apply a force to the tamper 217 and advance the compression element 280 along the placement rod 202 and/or the anchor support 210 in the direction of the second end 224 of the plug assembly 204. In one embodiment depicted in FIG. 5, slideable collar 280 may be substantially concentrically disposed about (e.g., about a circumference of) placement rod 202 and adjacent to sealing plug 240. In embodiments depicted in FIGS. 20 and 22, however, the sealing plug 240 is radially adjacent to or substantially concentrically disposed about the anchor support 210. The slideable collar 280 may be substantially concentrically arranged about the anchor support or the placement rod 202. Slideable collar 280 is moveably arranged with respect to placement rod 202 or anchor support 210. During deployment of the plug assembly 204, slideable collar 280 may be moved along the placement rod 202 and/or the anchor support 210 until entering, contacting, locking with, or engaging coupling feature 226. As the slideable collar 280 advances distally, it contacts, moves, compresses, and/or deforms the sealing plug 240. If the sealing plug is not already arranged adjacent to the anchor 208, the slideable collar 280 moves the sealing plug toward the anchor and may cause the sealing plug 240 to buckle or expand radially as it is compressed. Radial expansion of the sealing plug 240 may promote sealing of a puncture between the anchor element 208 and the sealing plug 240.

It will be appreciated by one of ordinary skill in the art having the benefit of this disclosure that prior to a successful deployment of the sealing plug, an insertion sheath may be properly positioned within a blood vessel (or another selected lumen). Proper placement of an insertion sheath may be accomplished with the aid of a puncture locator. Explaining further, according to one aspect, a puncture locator and insertion sheath are inserted through the hole in the vessel wall. The puncture locator may provide fluid communication path from a distal tip (where the insertion sheath enters the vessel) to a proximal end, where blood flow can be observed by an operator or the puncture locator may otherwise indicate proper placement of the distal tip within a blood vessel. Proper placement of the insertion sheath enables proper placement of the sealing plug or insertion of a vascular tool for another purpose. Any locating device and method may be used in conjunction with a puncture closure device according to principles described herein.

Figure 11:
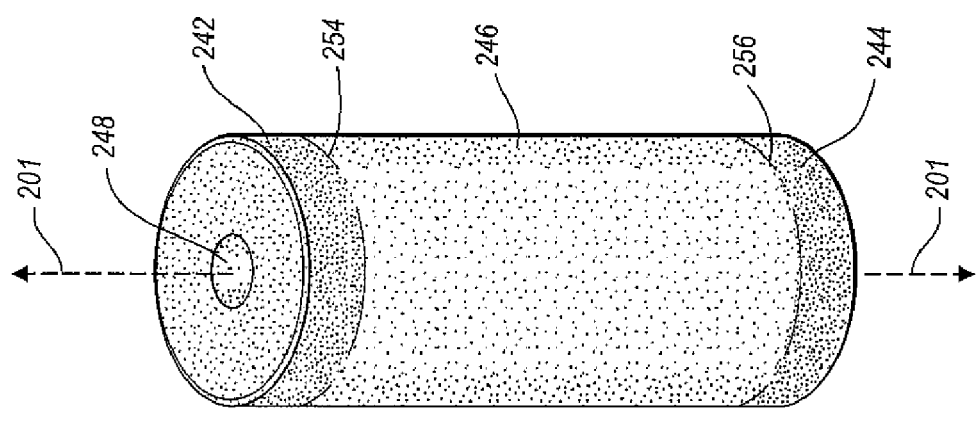
FIG. 11 shows a perspective view of a further embodiment of a sealing plug for use with a tissue puncture closure device according to the present invention.
Figure 10:
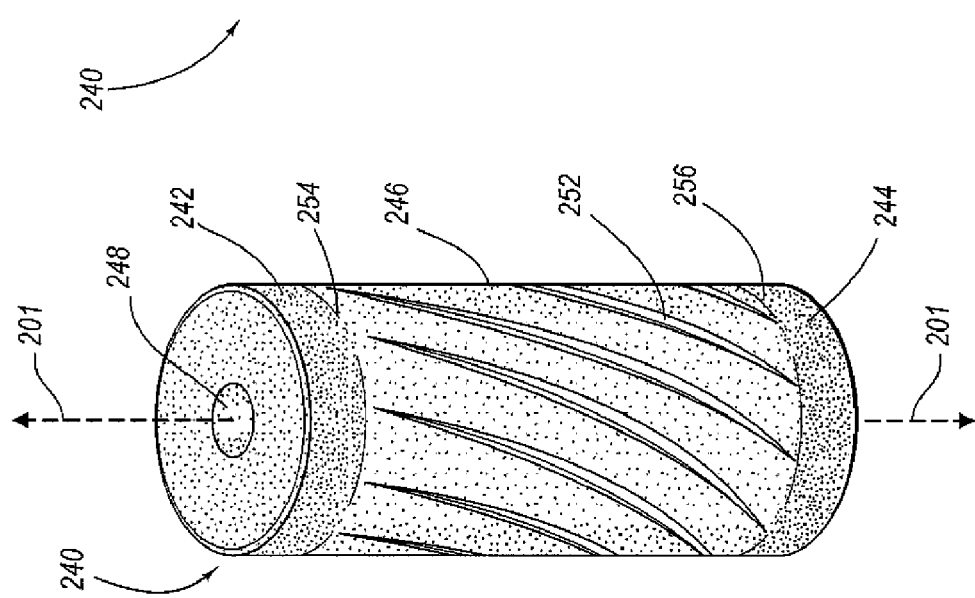
FIG. 10 shows a perspective view of another embodiment of a sealing plug for use with a tissue puncture closure device according to the present invention.
Figure 9:
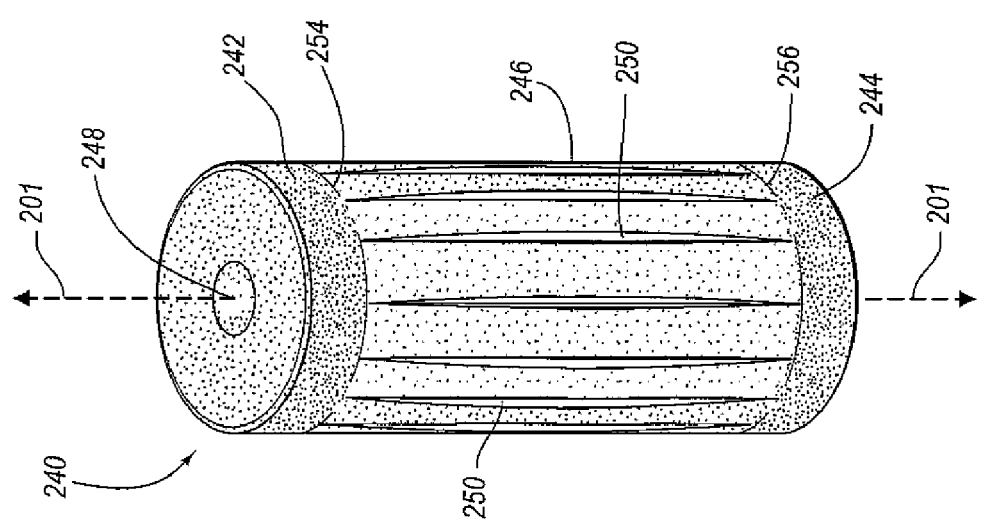
FIG. 9 shows a perspective view of one embodiment of a sealing plug for use with a tissue puncture closure device according to the present invention.
Figure 12:
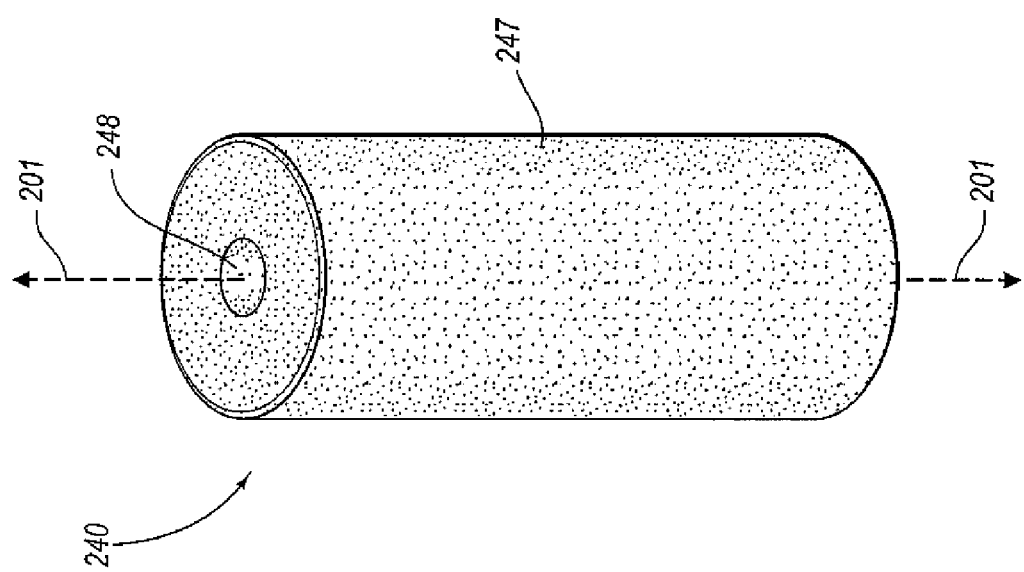
FIG. 12 shows a perspective view of an additional embodiment of a sealing plug for use with a tissue puncture closure device according to the present invention.

Turning to FIGS. 9-11, various embodiments of the sealing plug 240 are shown in respective perspective views. The sealing plug 240 may encompass any number of configurations, including the ones shown in FIGS. 9-11 that promote compression of the sealing plug 240 generally along longitudinal axis 201. Compression of the sealing plug 240 as shown in FIGS. 9-11 tends to cause the radial outward expansion with respect to longitudinal axis 201. When used in a puncture tract, such compression may cause sealing plug 240 to expand radially outwardly and sealingly engage or contact tissue surrounding the sealing plug 240. As shown in FIGS. 9-11, an end region 242 of the sealing plug 240 may comprise a relatively dense matrix of bioabsorbable material and may be positioned longitudinally adjacent to (along interfacial surface 254) an intermediate region 246 comprising a less dense bioabsorbable material than the end region 242. Intermediate region 246 is adjacent (along interfacial surface 256) an end region 244 comprising another relatively dense matrix of bioabsorbable material. Bore 248 may be formed through each of end regions 242, 244, and intermediate region 246. Further, bore 248 may be substantially centered about longitudinal axis 201. Regions 242 and 244, respectively, may be configured to facilitate compaction of layer 246 and corresponding radial expansion of region 246 by application of a compressive force between end regions 242 and 244 (i.e., toward intermediate region 246). Furthermore, as shown in FIG. 9, a plurality of slits such as substantially linear slits 250 may be formed at least partially into region 246 and may extend at least partially between interfacial surfaces 254 and 256. Optionally, linear slits 250 may be substantially parallel. Such linear slits 250 may promote radial expansion of region 246 in response to compression. Particularly, linear slits 250 may substantially inhibit or reduce development of hoop stress within region 246 that may resist radial expansion of region 246. In one embodiment shown in FIG. 10, a plurality of arcuate (e.g., helical) slits 252 may be formed at least partially into region 246 between interfacial surfaces 254 and 256. Also, as shown in FIG. 10, the plurality of arcuate slits 252 may extend substantially parallel to one another. In one embodiment, the plurality of arcuate slits 252 may extend in an intersecting (e.g., a so-called crisscross) fashion, may be unevenly spaced, or may be of unequal length. In one embodiment depicted in FIG. 11, sealing plug 240 may comprise end region 242, intermediate region 246, and end region 244 with no slits. In yet another embodiment depicted in FIG. 12, the sealing plug 240 may comprise uniform material 247. Of course, optionally, the sealing plug 240 may include linear slits, arcuate slits, or combinations of linear and arcuate slits as may be desired. Also, as shown in FIGS. 9-11, sealing plug 240 may be substantially cylindrical and a bore formed through the sealing plug 240 may also be substantially cylindrical. As mentioned above, sealing plug 240 can be made of animal derived collagens or synthetic type materials. Bore 248 of sealing plug 240 may be either molded, punched, machined, or otherwise formed. Although the sealing plug 240 is shown in FIGS. 9-12 as substantially cylindrical, any other shape may be used.

The bore formed through a bioabsorbable sealing plug may provide a structure that facilitates positioning of the sealing plug with respect to an anchor. Such a configuration may reduce the tamping distance applied to compress a sealing plug. Such a configuration may also reduce or eliminate tearing of a sealing pad during tamping and may promote more reproducible and reliable tamping and compression of a sealing plug.

Figure 14:
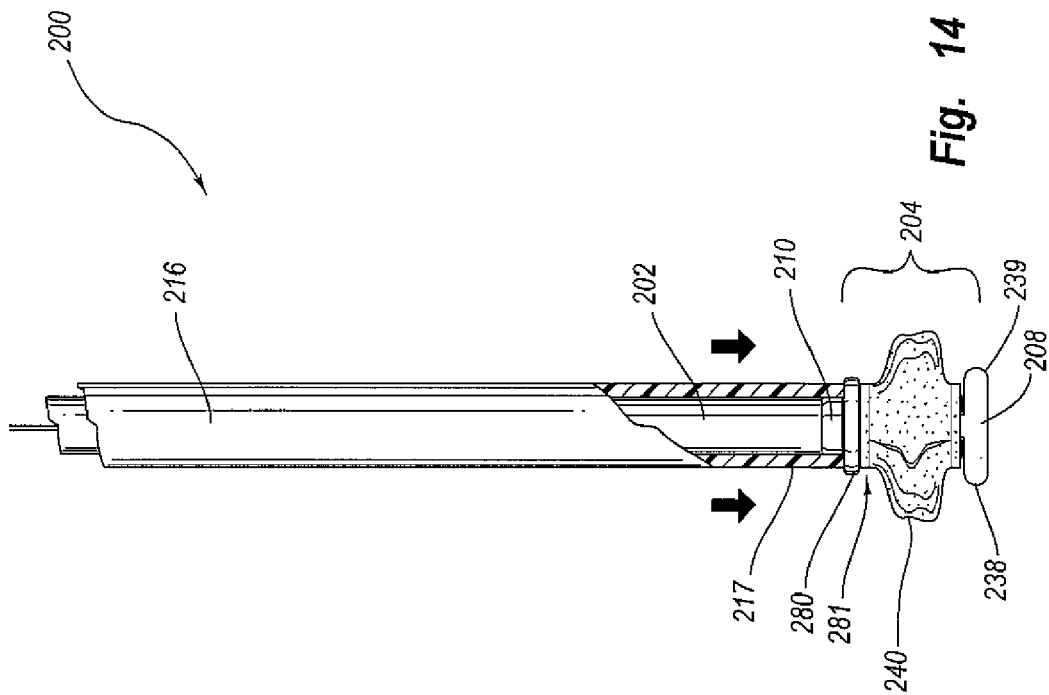
FIG. 14 shows a partial side view, partly in section, of the internal tissue puncture closure device shown in FIG. 13 following deployment of the plug assembly.
Figure 13:
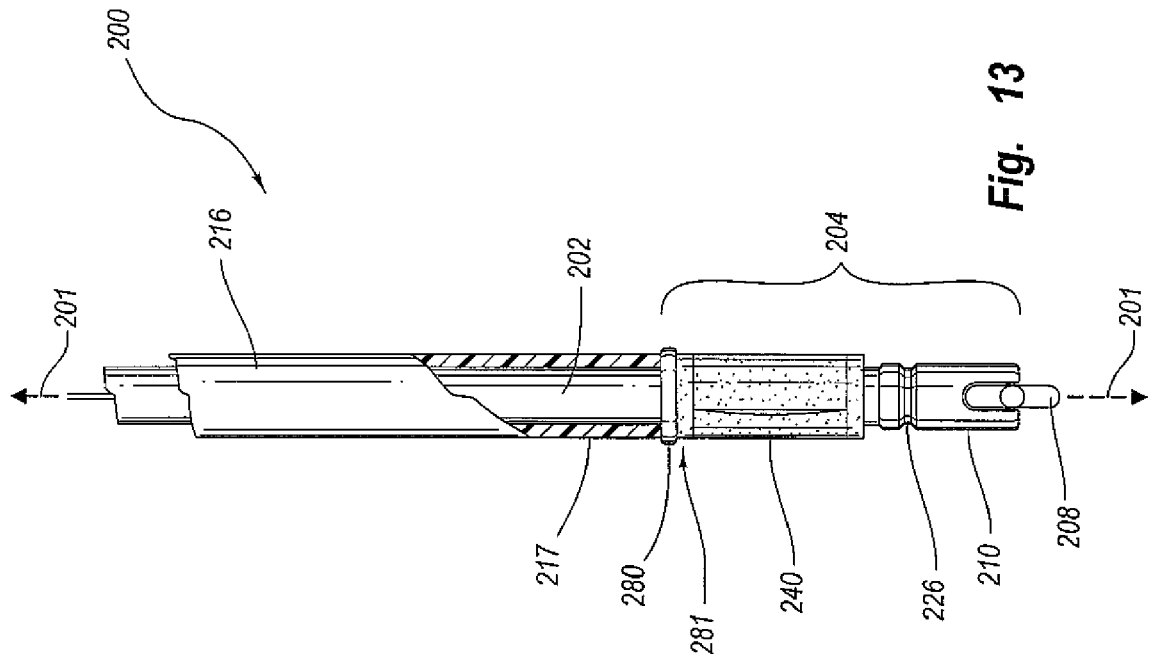
FIG. 13 shows a partial side view, partly in section, of an internal tissue puncture closure device prior to deployment of a plug assembly.
Figure 21A:
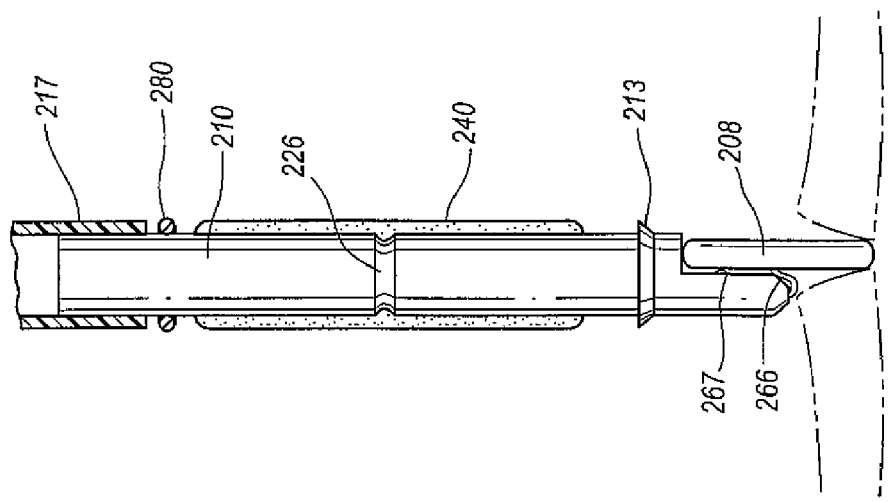
FIG. 21A is a partial cross-sectional view of the puncture closure device shown in FIG. 20.

More particularly, turning to FIG. 13, a portion of the puncture closure device 200 is shown in an initial or "ready to deploy" configuration, wherein each of the anchor support 210, sealing plug 240, tamper 217, and placement rod 202 are generally aligned along longitudinal axis 201. Following insertion of anchor 208 through a percutaneous tissue incision and into an arterial puncture or other lumen, the anchor 208 may be caused to rotate to the position shown in FIG. 14, such that its wings 238, 239 are arranged adjacent to an internal wall of the lumen to anchor puncture closure device 200 to the tissue breach (similar to the position of anchor 108 as shown in FIG. 2). The puncture closure device 200 may be twisted and/or pulled in a proximal direction to facilitate rotation of the anchor 208 to engage the lumen. Similar to the above-described operation of a conventional puncture closure device 100, the sheath 216 houses a tamper 217 for advancing the slideable collar 280 along the placement rod 202 toward the coupling feature 226 and toward the anchor 208. Tamper 217 may be driven manually (i.e., by hand) or with an automatic driving system to force slideable collar 280 toward the anchor 208. Accordingly, slideable collar 280 may engage or abut sealing plug 240 at a first or proximal end 281 of the sealing plug 240 to move the sealing plug 240 generally along longitudinal axis 201. Such movement of sealing plug 240 may be substantially concentric with respect to the placement rod 202 (and/or the support anchor 210). Further, such movement of sealing plug 240 may cause the bore of sealing plug 240 to become positioned about (e.g., substantially concentrically) at least a portion of the anchor support 210. Force applied to slideable collar 280 may compress sealing plug 240, as shown in FIG. 14. As the sealing plug 240 is compressed longitudinally generally between anchor 208 and slideable collar 280, it correspondingly expands radially against the surrounding tissue to secure the anchor 208 and seal a puncture. In two embodiments shown in FIGS. 20 and 22, a protruding lip 213 arranged on the anchor support 210 may limit the travel of the sealing plug 210 toward the anchor 208. In other embodiments, sealing plug 210 travel is only limited by the anchor 208.

In addition, the slideable collar 280 may be configured to couple to the coupling feature 226 formed in anchor support 210. More specifically, in one embodiment, the inner circumference of slideable collar 280, as shown in FIGS. 15-16 may include a plurality of inward radial protrusions 284. As slideable collar 280 moves toward and passes onto anchor support 210, sealing plug 240 is longitudinally compressed and radially expands in proximity to anchor 208. When slideable collar 280 reaches coupling feature 226, the plurality of protrusions 284 expand into and are captured (e.g., within a groove as shown in FIG. 15) or otherwise coupled to or locked in position with respect to the coupling feature 226. Slideable collar 280 may comprise a biologically resorbable material made of the materials mentioned above or others. In one embodiment shown in FIG. 20, the slideable collar 280 does not include inward radial protrusions 285. The slideable collar 280 is elastically expanded from a normal diameter to fit around the anchor support 210. When the slideable collar 280 reaches the coupling feature 226, it springs closer to or back to its normal diameter and resists removal from the coupling feature 226. In one embodiment shown in FIGS. 22-23B, the slideable collar 280 includes a pair of leg members 283 which are biased to press against the anchor support 210 as the slideable collar 280 is moved distally therealong. As shown in FIGS. 23A-23B, the leg members 283 abut the sealing plug 240 as the slideable collar 280 is advanced by the tamper 217 and assist in expanding the sealing plug.

Embodiments disclosed above may provide substantial centering of a sealing plug with respect to an anchor. Such configurations may facilitate proper positioning of the plug assembly 204 with respect to an arteriotomy. In addition, the embodiments described above may provide more reproducible and reliable tamping and less tearing of the sealing plug. Also, some of the disclosed embodiments which deposit a sealing plug assembly may eliminate the need to cut a suture near the surface of the patient's skin. Eliminating the need cut a suture may also reduce the risk of tissue tract infections by reducing or eliminating foreign material near the tissue tract opening.

Once the sealing plug 240 has been compressed, in some embodiments everything but the plug assembly 204 is removed from the tissue tract. Therefore, anchor support 210 may be operably and releasably connected to placement rod 202. A fastener, including, but not limited to: a threaded screw, a hook, an elastomeric stopper, an inflatable stopper, or the like, may be employed to selectively couple (and decouple) anchor support 210 to placement rod 202. In one embodiment depicted in FIG. 17, placement rod 202 may operably connect to anchor support 210 with a plug 276 positioned generally within cavity 214 and affixed to filament 274 (e.g., a suture, cord, hose, or other slender member). Plug 276 may be pliant and, therefore, may be forced into cavity 214 or removed therefrom. As shown in FIG. 17, filament 274 may extend through bore 278 of placement rod 202 and may be accessible to a user of the puncture closure device 200. Thus, placement rod 202 may be coupled to anchor support 210 if filament 274 is coupled to placement rod 202 and plug 276 is arranged inside cavity 214. The coupling of placement rod 202 to anchor support 210 may inhibit retracted longitudinal (i.e., away from anchor 208, along longitudinal axis 201) movement of the placement rod 202 with respect to anchor support 210. Plug 276 may be elastomeric and shaped to resist removal from cavity 214 under normal conditions of placing the plug assembly 204. Moreover, in one embodiment, filament 274 may comprise a fluid conducting tube which may be pressurized to inflate plug 276 into an expanded shape and couple placement rod 202 to anchor support 210.

Likewise, anchor support 210 may be selectively released from placement rod 202. In one embodiment, following deployment of the plug assembly 204 and coupling of slideable collar 280 to coupling feature 226 (as depicted in FIG. 18), placement rod 202 can be disconnected from the anchor support 210. As described above, plug 276 may be pliant, compressible, or otherwise configured so that when a force exceeding a selected minimum force is applied to filament 274 in a retraction direction (i.e., away from anchor 208), the plug 276 deforms to pass through the upper cylinder segment 270 of cavity 214. In embodiments wherein filament 274 comprises a fluid conducting tube, plug 276 may be deflated to be removed from cavity 214. Thus, placement rod 202 and anchor support 210 may be selectively connected and disconnect as desired.

In one embodiment, after the slideable collar 280 is coupled to coupling feature 226 and the placement rod 202 is disconnected from the anchor support 210, each of the placement rod 202, the tamper 217, the filament 274, the plug 276 and the sheath 216 may be withdrawn from percutaneous tissue defining an incision. More particularly, from the foregoing discussion, it may be appreciated that the plug assembly 204 may remain within a patient to close a vascular puncture. For example, FIG. 19 shows plug assembly 204 anchored proximate to wall 234 of blood vessel 290 and positioned at least partially within percutaneous incision 219 (i.e., surrounded by percutaneous tissue 220) to effectively close puncture 218. As shown in FIG. 19, sealing plug 240 may be expanded against the surrounding percutaneous tissue 220 and substantially centered with respect to the original lumen puncture 218.

The embodiments shown in FIGS. 20-21D and 22-23B illustrate similar deployment of the sealing plug 240 by actuating the sliding collar 280 with the tamper 217. In each of these two embodiments, when the anchor 208 is deployed in a lumen or vessel, the sealing plug 240, which is arranged about the anchor support 210, is compressed by the sliding collar 280. The sliding collar 280 may likewise be arranged around the anchor support 210. The tamper 217 is forced distally, which advances the sliding collar 280 and compresses and causes radial expansion of the sealing plug 240. The sealing plug 240 may only advance to the lip 213, and further advancement of the sliding collar 280 may tend to cause only radial expansion of the sealing plug 240. The sliding collar 280 may be advanced until it reaches the radial groove or coupling feature 226 of the anchor support 210. The sliding collar 280 then contacts and locks in the coupling feature 226 and prevents retraction of the sealing plug 240. The anchor support 210, sealing plug 208, sliding collar 280, and the anchor 208 remain at the puncture side and seal the puncture.

While certain embodiments and details have been included herein for purposes of illustrating aspects of the invention, it will be apparent to those skilled in the art that various changes in the systems, apparatuses, and methods disclosed herein may be made without departing from the scope of the invention, which is defined by the appended claims. Moreover, features shown in certain embodiments are not exclusive to the embodiment shown. Any feature shown in any embodiment may be used in any combination with other features described herein.

What is claimed is:

1. A puncture closure device, comprising:
    an anchor support including a coupling feature and a rigid portion;
    an anchor connected to the anchor support, wherein the anchor is configured for insertion through a puncture;
    a movable compression element configured to be movable between a first position and a second position, wherein movement of the compression element to the second position causes coupling of the compression element to the coupling feature of the anchor support;
    a removable placement rod coupled to a first end of the anchor support;
    a sealing plug positioned generally between the compression element and the anchor, the compression element being movable towards the anchor along a portion of the anchor support and along a portion of the removable placement rod, each of the anchor support and removable placement rod extending within at least a portion of the sealing plug;
    wherein the compression element is configured to cause compression of the sealing plug generally between the compression element and the anchor upon movement of the compression element from the first position to the second position, and the anchor support with the compressed sealing plug being releasable from the removable placement rod.

2. The puncture closure device of claim 1, wherein the anchor support further comprises a first recess and a second recess, the first recess being located near the first end of the anchor support and the second recess being located at a second end of the anchor support.

3. The puncture closure device of claim 2, wherein the anchor is pivotably connected to the anchor support and at least a portion of the anchor is positionable within the second recess by pivoting of the anchor.

4. The puncture closure device of claim 3, wherein the anchor is pivotably connected to the anchor support with a pin.

5. The puncture closure device of claim 3, wherein the anchor is pivotably connected to the anchor support with a suture.

6. The puncture closure device of claim 2, wherein the removable placement rod is coupled to the anchor support by a plug affixed to a filament, wherein the plug is removably positioned within the first recess of the anchor support.

7. The puncture closure device of claim 6, wherein the plug is pliant or inflatable.

8. The puncture closure device of claim 2, wherein the compression element is a ring-shaped element positioned about a portion of a circumference of the removable placement rod.

9. The puncture closure device of claim 8, wherein the sealing plug has a bore positioned generally about a portion of the circumference of the removable placement rod.

10. The puncture closure device of claim 9, wherein the sealing plug comprises collagen.

11. The puncture closure device of claim 1, wherein the sealing plug has a bore positionable generally about a portion of the circumference of the anchor support.

12. The puncture closure device of claim 11, wherein movement of the compression element from the first position to the second position is intended to cause the bore of the sealing plug to be positioned generally about a portion of the circumference of the anchor support.

13. The puncture closure device of claim 11, wherein the sealing plug comprises collagen.

14. The puncture closure device of claim 1, wherein each of the anchor support, the anchor, the sealing plug, and the compression element comprises a biologically resorbable material.

15. The puncture closure device of claim 1, wherein the sealing plug is at least partially positioned on the removable placement rod when the movable compression element is in the first position and entirely positioned on the anchor support when the movable compression element is in the second position.

16. A puncture closure assembly comprising:
an insertion sheath configured to receive at least a portion of a puncture closure device; wherein the puncture closure device comprises:
an anchor support including a coupling feature and a rigid portion;
an anchor connected to the anchor support, wherein the anchor is configured for insertion through a tissue wall puncture;
a movable compression element configured to be movable between a first position and a second position, wherein movement of the compression element to the second position causes coupling of the compression element to the coupling feature of the anchor support;
a removable placement rod coupled to the anchor support, at least a portion of the compression element being positioned on the removable placement rod in the first position;
a sealing plug positioned generally between the compression element and the anchor, the compression element being movable towards the anchor along a portion of the anchor support and along a portion of the removable placement rod, each of the anchor support and removable placement rod extending within at least a portion of the sealing plug;
wherein the compression element is configured to cause compression of the sealing plug generally between the compression element and the anchor upon movement of the compression element from the first position to the second position, the anchor support being releasable from the rigid support member removable placement rod to dispose the sealing plug at the tissue wall puncture.

17. The puncture closure assembly of claim 16, wherein the sealing plug has a bore positionable generally about a portion of the circumference of the anchor support.

18. The puncture closure assembly of claim 17, wherein movement of the compression element from the first position to the second position is intended to cause the bore of the sealing plug to be positioned generally about a portion of the circumference of the anchor support.

19. The puncture closure assembly of claim 17, wherein the sealing plug comprises collagen.

20. The puncture closure assembly of claim 16, wherein the sealing plug is at least partially positioned on the removable placement rod in the first position and entirely positioned on the anchor support in the second position.

21. An assembly for sealing an incision or puncture in a body of a patient wherein the incision or puncture extends through the tissue of the patient into a blood vessel, duct, or lumen of the patient, the assembly comprising:
a puncture closure device, the closure device comprising:
an anchor formed of bioabsorbable material and sized to be positioned in the blood vessel, duct, or lumen of the patient;
a generally rigid elongate member formed of bioabsorbable material;
a removable placement rod releasably coupled to the generally rigid elongate member;
the rigid elongate member and the removable placement rod extending within a compressible member formed of bioabsorbable material, the bioabsorbable material being slidably positioned along the rigid elongate member and removable placement rod;
wherein the anchor, rigid elongate member, and compressible member are releasable from the removable placement rod at the incision or puncture.

22. An assembly according to claim 21, further comprising a retaining ring slidably positioned on the rigid elongate member proximal of the compressible member.

23. An assembly according to claim 21, further comprising:
a retaining ring slidably positioned on the rigid elongate member proximal of the compressible member;
a groove receptive of the retaining ring disposed in the rigid elongate member.

24. An assembly according to claim 21 wherein the compressible member is concentric with the rigid elongate member and arranged around the rigid elongate member.

* * * * *